United States Patent

Fenner et al.

[11] Patent Number: 5,563,341
[45] Date of Patent: Oct. 8, 1996

[54] VAPOR PRESSURE SENSOR AND METHOD

[76] Inventors: Ralph L. Fenner, 978 Peutz Valley Rd., Alpine, Calif. 91901; Robert C. Quinn, 3797 Mosswood Dr., Lafayette, Calif. 94549

[21] Appl. No.: 474,241

[22] Filed: Jun. 7, 1995

[51] Int. Cl.⁶ .................................................. G01N 19/10
[52] U.S. Cl. ........................................................ 73/335.11
[58] Field of Search ............................... 73/29.01, 29.02, 73/335.02, 335.05, 335.11, 335.13, 24.04, 514.23, 514.36, 514.37

[56] References Cited

U.S. PATENT DOCUMENTS

| | | | |
|---|---|---|---|
| 2,461,310 | 2/1949 | Cilley | 73/335.05 |
| 3,077,774 | 2/1963 | McIlvaine | 73/335.05 |
| 3,301,057 | 1/1967 | Smith et al. | 73/335.05 X |
| 4,969,359 | 11/1990 | Mikkor | 73/514.36 |
| 5,048,336 | 9/1991 | Sugihara et al. | 73/29.01 |

FOREIGN PATENT DOCUMENTS 0158289  12/1979  Japan ..................... 73/335.11

*Primary Examiner*—Michael Brock
*Attorney, Agent, or Firm*—Flehr, Hohbach, Test, Albritton & Herbert

[57] ABSTRACT

A vapor pressure sensor comprising a substrate having a body with first and second planar parallel surfaces. A hole is formed in the body and extends through and between the first and second surfaces. A beam is disposed in the hole in the body and is formed integral with the body and forms a junction with body and is formed as a cantilever in the hole in the body. The beam has a surface. A vapor adsorbing coating is carried by the surface of the beam and the coating is substantially uniform in thickness. It is adhered to the surface of the beam and is fully shear restrained by the beam. A strain measuring device is carried by the substrate and disposed at the junction between the body and the beam to measure shear forces placed in the beam by the vapor adsorbing coating. The vapor adsorbing coating expands and contracts in directions parallel to the surface of the beam as the vapor adsorbing coating adsorbs and desorbs vapor.

8 Claims, 2 Drawing Sheets

VAPOR PRESSURE SENSOR AND METHOD

This invention relates to vapor pressure sensor method and more particularly to such a sensor and method which utilizes the elongation properties of porous organic and inorganic materials to sense vapor pressure and the coupling of these elongation properties to a strain gauge for the purpose of measuring relative vapor pressure as for example humidity.

Sensors for gauging humidity have heretofore been provided and have utilized oxidized porous silicon as a moisture adsorbing dielectric between two electrodes of a capacitor. Water vapor permeating the porous volume between the electrodes results in a net change in the dielectric constant which is monitored to measure the capacitance of the device to give a measure of change in humidity. Its disadvantage is that its output is not a straight line. In addition, since it measures mass and mass is not a parameter that stops at any point, the measurement does not stop at 100% relative humidity but continues to increase as the moisture content of the porous silicon increases. Hygrometers have heretofore been made utilizing polymers known to swell in the presence of water vapor. Natural and synthetic polymers have been used. The swelling of unrestrained or partially restrained natural and synthetic polymers is known to follow a non-linear absorption pattern as substantial hysteresis exists between adsorb and desorb. The mass adsorption of moisture by natural and synthetic polymers and the detection of change in capacitance is disadvantageous because the mass adsorption of water is not limited by the phase change from vapor-to-liquid, and therefore humidity detection at 100% relative humidity/water transition point is indeterminant by such mass detecting systems.

Such sensors are also subject to repeatability errors. Humidity sensing elements of this type have generally been large, difficult and expensive to manufacture. There is therefore a need for a new and improved vapor sensor and method for measuring vapor pressure which overcomes these disadvantages.

In general it is the object of the present invention to provide a vapor pressure sensor by which elongation properties of porous organic and inorganic materials are utilized to sense vapor pressure.

Another object of the invention is to provide a sensor and method of the above character in which the elongation properties are sensed by a strain gauge to provide a measure of vapor adsorption and desorption.

Another object of the invention is to provide a sensor and method of the above character in which substantial linearity is achieved with freedom from hysteresis and with repeatable results.

Another object of the invention is to provide a sensor and method of the above characteristics which can be utilized to measure relative vapor pressure of any gas which is adsorbed selectively by a substrate to produce a stress which can be induced into an adnate member held in full shear restraint.

Another object of the invention is to provide a sensor and method of the above character which makes possible miniaturization.

Another object of the invention is to provide a sensory and method of the above character which can be massed produced at low cost.

Additional objects and features of the invention will appear from the following description in which the preferred embodiments are set forth in detail in conjunction with the accompanying drawings.

Figure 1:
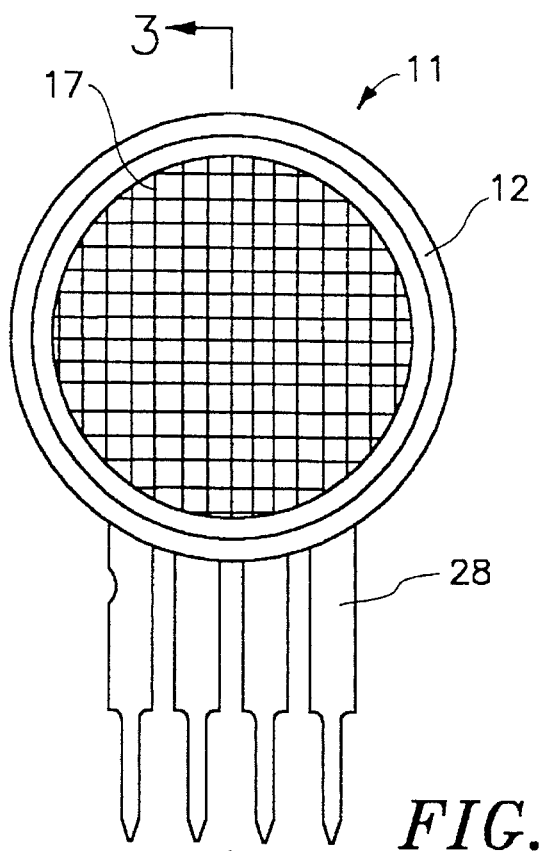
FIG. 1 is a top plan view of a vapor pressure sensor incorporating the present invention.
Figure 2:
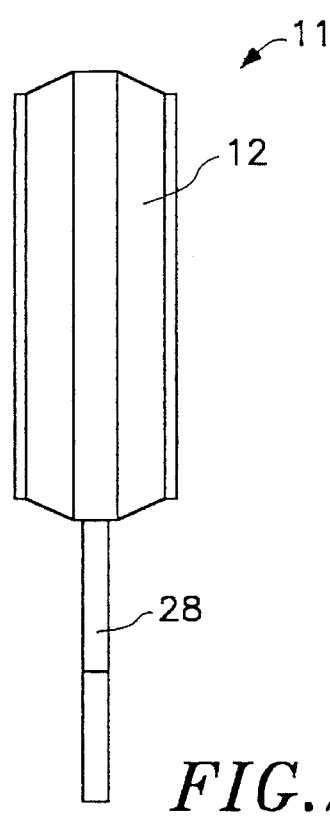
FIG. 2 is a side elevation view of the vapor pressure sensor shown in FIG. 1.
Figure 4:
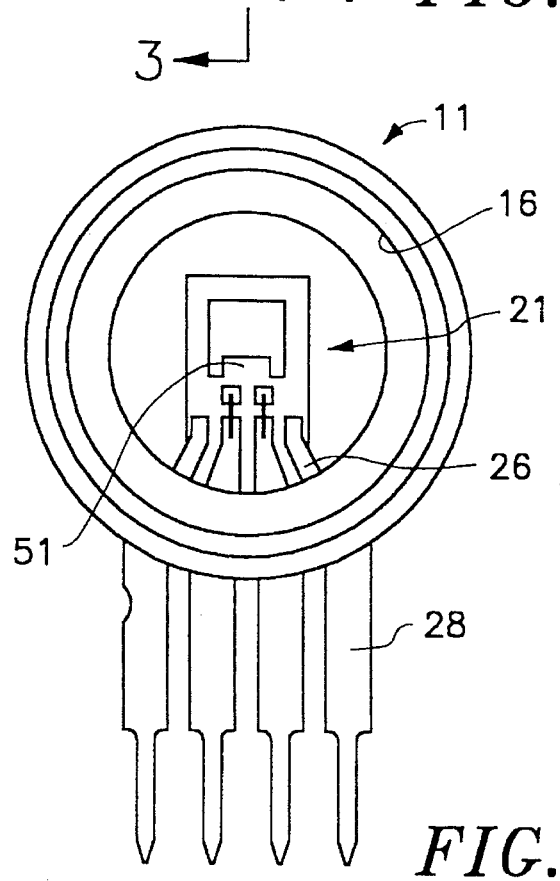
FIG. 4 is an enlarged top plan view of the sensor shown in FIG. 1 with the protective screen removed.
Figure 3:
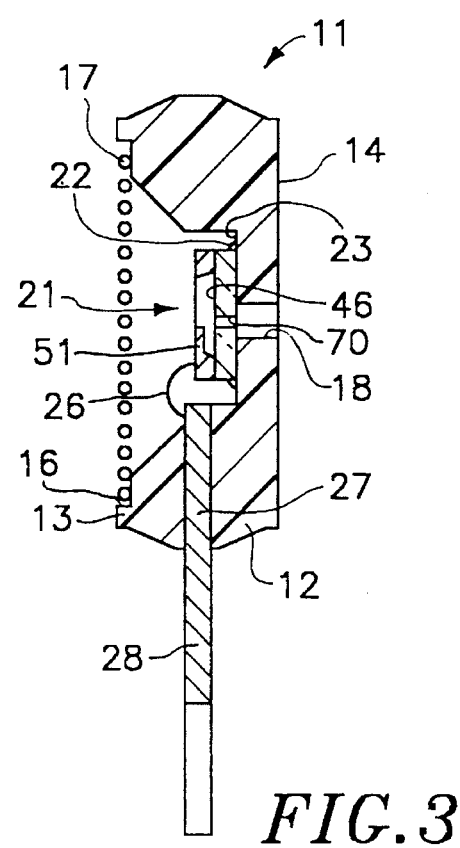
FIG. 3 is a cross-sectional view of the vapor pressure sensor shown in FIG. 1.

In general, the vapor pressure sensor incorporating the present invention consists of a housing or case having die mounted therein. The die is formed of a silicon body having first and second surfaces of said body being formed with a cavity extending from the second surface to the first surface. The body has a cantilevered portion integrally formed therewith which extends over the cavity so that it is cantilevered over the cavity. The cantilevered portion has a thickness substantially less than the thickness of the body and a length substantially less than the width. A thin vapor adsorbing coating is applied to said surface over said cantilevered portion. The vapor adsorbing coating is securely adhered to said first surface and is fully shear restrained by said cantilevered portion. The coating responds to changes in relative vapor pressure from the environment by swelling in directions parallel to the first surface. The swelling of the coating causes stress deformation of said cantilevered portion. Means is carried by the housing and secured to the die for measuring said stress deformation of the cantilevered portion to provide a measure of relative vapor pressure.

More particularly as shown in FIGS. 1 through 6 of the drawings the vapor pressure sensor 11 incorporating the present invention consists of a housing or a disk-like case 12 formed of a suitable material, such as a molded plastic and having top and bottom sides 13 and 14. It is provided with a generally cylindrical recess 16 which opens through the top side 13. A circular screen 17 is mounted in the top side 13 and covers the recess 16 as shown particularly in FIG. 3 but permits the recess 16 to be exposed to the environment in which the sensor 11 is located. If desired, an additional hole 18 can be provided extending through the bottom side which opens into the recess 16 to further ensure that the recess 16 is exposed to the environment. The hole 18 also ensures that any moisture collected will drain out and thus prevent the formation of a well.

A semiconductor device or die 21 is disposed within the recess 16 and is mounted in a suitable manner therein such as by utilizing a silicon RTV die bond material 22 to secure it to the bottom wall 23 of the recess 16. The die 21 is secured by a plurality of leads which are wire bonded to the die 21 and to a lead frame 27 molded into the case or housing 12. The lead frame 27 includes a plurality of spaced apart leads 28 lying in a plane and extending in one direction outside the case or housing 12.

The sensor device or die 21 consists of a body 31 which serves as a rigid substrate and having planar and parallel upper and lower surfaces 32 and 33. The body is formed of a suitable material such as n-type crystalline silicon having a desired orientation, as for example a (100) crystallographic surface orientation and a (110) orientation for the sides. As shown particularly FIGS. 5 and 6, the body 31 has a diffused strain gauge 36 diffused through the top or upper surface 32 in a predetermined location for purposes hereinafter described. Such a diffused strain gauge 36 can be formed in a conventional manner by appropriate photographic and diffusion techniques. Similarly, low-resistance interconnects 38 are diffused through the surface 32 and are connected to the strain gauge 36 and make connections to metal pads 39. The metal pads 39 are formed of suitable material such as aluminum and are disposed over the surface 32 and insulated therefrom by an insulating layer 41 of a suitable material such as silicon dioxide. The pads 39 provide interconnect regions for the gold leads 26 hereinbefore described making connection to the lead frame 27.

Figure 5:
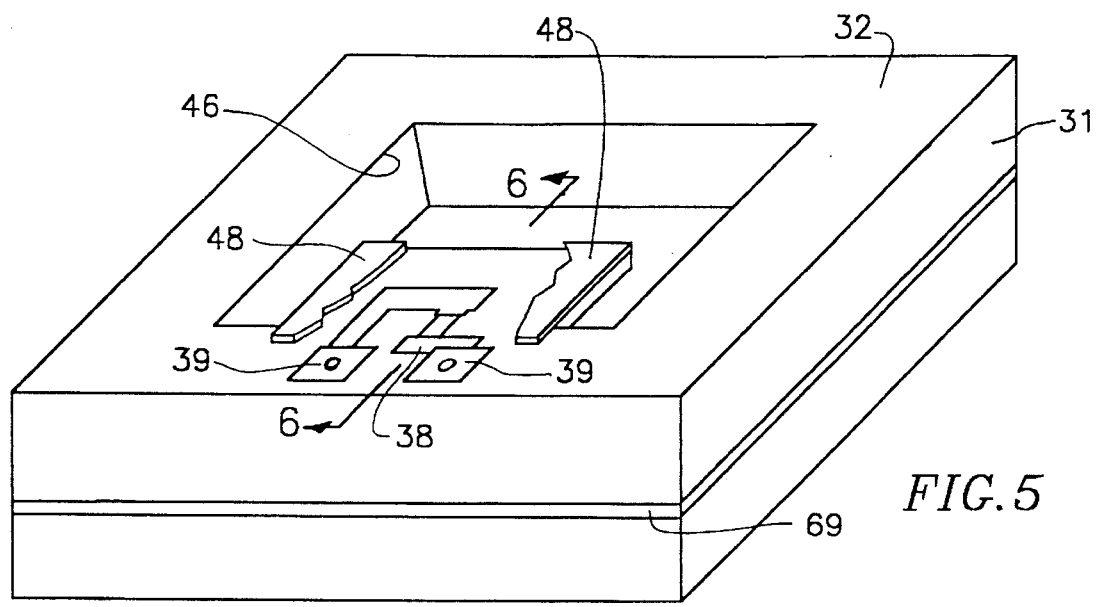
FIG. 5 is an isometric view of the die utilized in the sensor shown in FIGS. 1 through 4.
Figure 6:
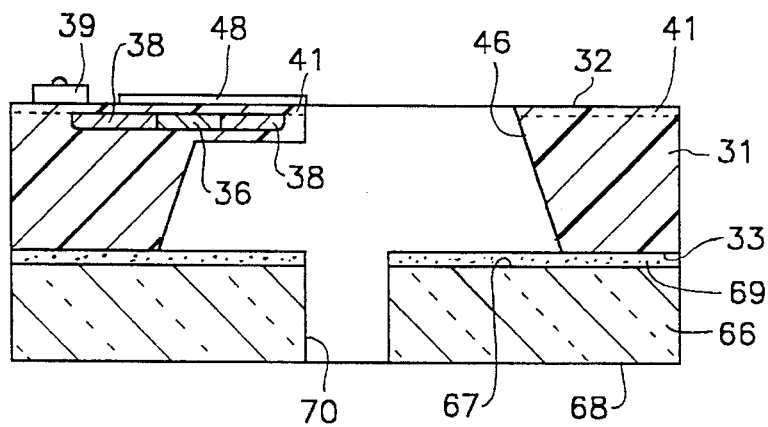
FIG. 6 is a cross-sectional view taken along the line 6—6 of FIG. 5.

A recess or hole 46 is formed in the body 31 from the second or lower surface 33 and within the confines of the outer perimeter of the body 31 in a suitable manner such as by micromachining or chemical etching. The recess 46 is formed to a depth so that there remains a thin diaphragm which is integral with the body 31 of a suitable thickness, as for example ranging from 5 to 100 microns and preferably 10–50 microns. If the recess 46 is formed by chemical etching such as an anisotropic etch, it would have tapered sidewalls as determined by the crystalline material of the silicon body 31 as shown in FIGS. 5 and 6. The diaphragm would be formed with its surfaces lying in the (100) planes and being bounded at its edges by (111) planes.

A vapor adsorbing coating 48 is carried by and extends over the surface 32 of the body 31. The coating 48 should be of uniform thickness. Also it should firmly adhered to the surface 32 and be fully shear restrained thereby. The coating 48 should be formed of a material which responds to any gas in which the relative vapor pressure varies from 0 to 100 and which is adsorbed and desorbed and will expand and contract radially from any direction parallel to the plane of the surface 32 to exert hygrostress forces. The resultant forces strain or deform the surface to thin it out (increase resistance) or thicken (decrease resistance) of the reactive substrate. The consequence of the present invention is to maximize the strain deformation induced by hygrostress. The thinning and thickening of the imbedded strain measuring gauge 36 results in the transduction of hygrostress to measurable hygrostrain. The coating 48 is therefore used for transducing a relative vapor pressure into shear stress and then into strain which is measured to provide a measurement from zero to 100 ratio which is linear, hysteresis free and repeatable.

A number of materials have been found to exhibit satisfactory characteristics within the above defined parameters and can include natural and synthetic organic materials which can include sulfones, polyimides, cellulose-based materials, chitin, poly(amide)-imide, etc. A porous coating of inorganic glass or silicon will provide a vapor pressure response. This effect can be enhanced by zeolite-type materials which are selective to the moisture molecule. One material found to be particularly satisfactory is SRDL/PAL 5552 polyimides. Another material is EPO-TEK 600/670. The polyimide was applied in liquid form onto a wafer from which die are to be made by a suitable means such as a spin coater rotating at a speed of 3000 rpm for 60 seconds to provide a coating having a thickness ranging from 1 to 10 microns and preferably 2 to 5 microns and thereafter cured at 120° C. for 20 minutes to partially cure the coating. Since the coating covers the entire wafer, it is necessary to remove those areas of the surface on which it is not desired. This is accomplished by a process of spin coating a photoresist and exposing through a mask and subsequently developing and etching the unwanted polyimide away. The polyimide is then cured at high temperature, 130° C., for 15 minutes followed by a temperature of 200° C. for 30 minutes and 400° C. for 30 minutes to fully cure the coating.

The polyimide coating applied in this manner has a very uniform thickness and good adhesion throughout. In order to enhance the adhesion of the coating to the surface 32, a suitable bonding agent such as DuPont VM651 Adhesion Promoter can be applied to the surface 32 and thereafter dried after which the polyimide coating hereinbefore described can be applied in the manner hereinbefore described.

As soon as the coating 48 has been applied, a portion of the material forming the diaphragm is removed in a suitable manner such as by chemical etching or by micromachining to form a hole adjoining the recess 46 extending between and through surfaces 32 and 33 to provide a diaphragm portion which forms a cantilevered beam 51. As shown in FIG. 5 and 6, the recess 46 can have a rectangular configuration as can the cantilevered beam 51. The cantilevered beam 51 has three sides which are free and thus the beam is only attached on one side and is a formed integral with the body 31. In accordance with the present invention, it has been found that it is desirable to provide a cantilever beam which has a length that is substantially less than the width. The width should be 5 to 10 times the length of the cantilever beam 51. Choosing such dimensions for the cantilever beam 51 has a number of advantages. It reduces the influence of pressure and acceleration on the beam 51. It also increases the resonant frequency so that it will be less sensitive to vibrations and shock.

The recess 46 in the body 31 into which the cantilevered beam 51 extends is formed so that the junction, a high stress point, between the cantilevered beam 51 and the sidewall of the body 31 forming the recess 46 immediately underlies one end of the diffused strain gauge 36 carried by the cantilevered beam. Thus, the strain gauge 36 is located in an optimum position to measure the stress applied to the cantilevered beam 51.

In order to form the cantilever beams 51, it may be desirable to remove all portions of the coating 43 which are not part of the cantilever beam 51. This can be accomplished by any suitable means such as photochemical etching or laser cuttings. Preferably, the coating 43 should extend over the body 31 to a region which clears the pads 39. After the wafer has been process as hereinbefore described, the wafer can be die cut in a conventional manner into individual die to be utilized in the sensors of the present invention.

As shown in FIGS. 5 and 6, the body 31 can be affixed to a support or constraint member 66 formed of a suitable material such as quartz or glass and which is provided with first and second surfaces 67 and 68 which are planar and parallel. The first surface 67 is bonded to the second surface 33 of the body 31 in a suitable manner such as by a glass frit seal 69. A hole 70 is formed in the support member 66 and serves to prevent collection of moisture in the recess or hole 46.

As soon as the die 21 has been completed it can be mounted on the bottom wall 23 of the case or housing 12 by the RTV die bond material 22. Thereafter, the gold leads 26 can be bonded to the pads 37 and to the lead frame 27 which is carried by the molded case or housing 12. The screen 17 can then be secured in place by a suitable means such as an adhesive. It can be seen that the die 21 is mounted in such a manner so that the coating 61 is exposed to ambient or to the environment through the holes in the screen 17.

Operation and use of the vapor pressure sensor 11 for sensing vapor pressure in accordance with the method of the present invention may now be described as follows. Let it be assumed that the vapor pressure sensor 11 has been placed in an environment in which it is desired to sense water vapor and that the sensor 11 has been connected to appropriate instrumentation. The sensor, if desired, may be temperature compensated in a conventional manner. When exposed to water vapor, the sensor was capable of measuring relative humidity from zero to 100% with substantially no hysteresis. The measurement results were repeatable. The response time was fast from 10 to 50 seconds and was self-limiting in that the ratio did not fall below zero when dry or exceed 1 at 100% relative vapor pressure.

The sensor was stable at saturation (100% relative humidity) and hygrostress approached dynamic zero as defined by the forces at equilibrium moisture or equilibrium water activity saturation. No further strain developed as a result of hygrostress during the shift from vapor to liquid. It is believed that with these measurements made with water vapor that it is possible to measure relative partial vapor pressure of any compound that induces hydrogen bonding stress response in polymers.

In connection with the foregoing it can be seen that the silicon body 31 provides a substrate which makes it possible to measure strain. Silicon is a material particularly suited for this purpose since diffused strain gauges can be provided therein. However, it should be appreciated that other substrate materials can be utilized and separate strain gauges can be mounted on the substrate to make the required strain measurements. For example, germanium can have epitaxially deposited gauges imbedded therein. The vapor pressure detecting layer can be any of a wide variety of adsorbing surfaces from chitin to porous glass.

It is important that the vapor adsorbing coating 61 be securely bonded to the silicon substrate by forming an intimate bond between the coating and the substrate without effecting the hygromechanical and piezoresistive performance of the vapor pressure sensor.

Figure 7:
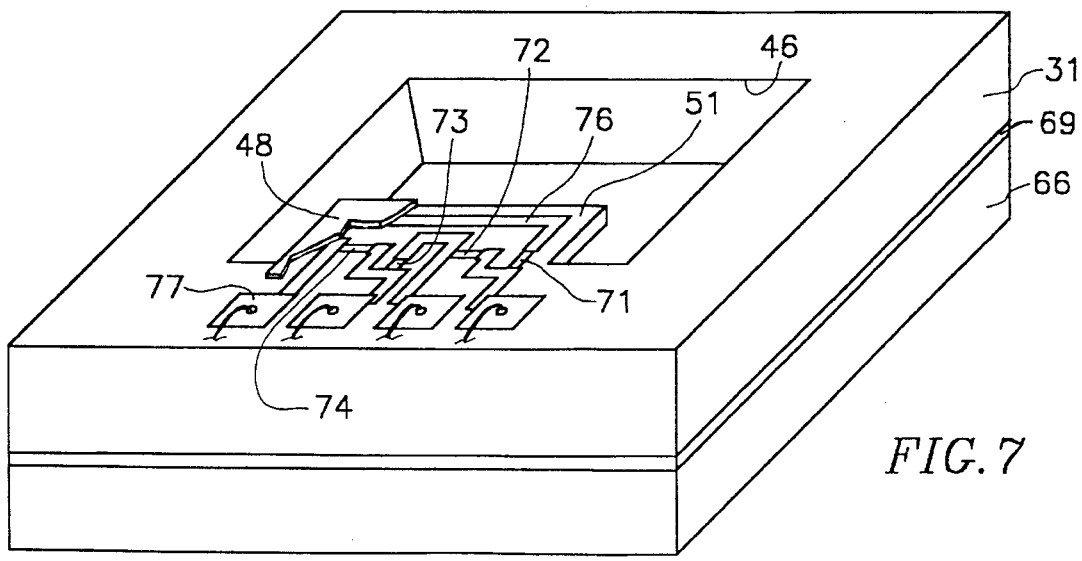
FIG. 7 is an isometric view of a full bridge arrangement of the vapor pressure sensor of the present invention.

Another embodiment of the vapor pressure sensor incorporating the present invention is shown in FIG. 7. The vapor pressure sensor of the present invention can be implemented in either a half or a full bridge configuration. A full bridge configuration is shown in FIG. 7 in which four strain gauges 71, 72, 73 and 74 of the type hereinbefore described have been provided in place of the single strain gauge 36 in FIGS. 5 and 6. The strain gauges 71–74 are all located in close proximity of the junction between the cantilevered beam 51 and the body 31 and achieve optimum performance. Two of the strain gauges 72 and 74 extend parallel to the junction wherein the other two gauges 71 and 73 extend at right angles to the junction and parallel to the longitudinal axis of the cantilever beam. The strain gauges 71–74 are connected as shown in FIG. 7 into a full bridge by diffused interconnects 76 and are also connected in the same manner to four output pads 77 which can be connected to the four leads 26 in the manner hereinbefore described. The full bridge arrangement of the present invention lends itself to temperature compensation in a manner well known to those skilled in the art, since some of the temperature effects are cancelled in the bridge itself.

In view of the foregoing it can be seen that there has been provided a vapor pressure sensor and a method for sensing relative humidity from zero to 100% substantially free of hysteresis and with repeatable results. The hygrostrain detected is at the molecular level and makes possible the fabrication of extremely small sensors. A low impedance resistive linear output is provided. The linear output of zero to 100% relative humidity is self-limiting. It has a low temperature coefficient. The sensor device is very small in size. It is resistant to contamination and if necessary it can be readily cleaned. It also can be manufactured by mass production techniques at a relatively low cost.

What is claimed is:

1. A vapor pressure sensor comprising a substrate, said substrate having a body having first and second planar parallel surfaces and a hole formed in the body extending through the first surface and between the first and second surfaces, a beam disposed in the hole in the body and being formed integral with the body and forming a junction with body and being formed as a cantilever in the hole in the body, the beam having a surface, a vapor adsorbing coating carried by said surface of the beam, said coating being substantially uniform in thickness and being adhered to said surface of the beam and being fully shear restrained by the beam, a strain measuring device carried by the substrate and disposed at the junction between the body and the beam to measure shear forces placed the beam by the vapor adsorbing coating, said vapor adsorbing coating having the characteristic that it expands and contracts in directions parallel to the surface of the beam as the vapor adsorbing coating adsorbs and desorbs vapor.

2. A sensor in claim 1 wherein said substrate is formed of silicon and wherein said vapor adsorbing coating is a polyimide.

3. A sensor as in claim 1 together with a case having a recess therein, a lead frame carried by the case and extending into the recess, said substrate being in the form of a die disposed in the recess in the case and lead means connecting the lead frame to the shear measuring device, said recess being open to the environment so that the coating is exposed to the environment and can measure vapor pressures present in the environment.

4. A sensor as in claim 1 wherein said strain measuring device forms a part of a bridge.

5. A vapor pressure sensor comprising a substrate formed of silicon, portions of said substrate being removed to form a thin flexible cantilevered beam having a surface and forming a junction with the substrate, a vapor adsorbing and desorbing coating carried by said surface and being firmly adhered to said surface of said beam so that it is shear restrained by said beam, said coating responding to changes in relative vapor pressure by swelling in a longitudinal direction parallel to the surface of the beam to cause said beam to be deformed and means for measuring the deformation of said cantilever beam at said junction.

6. A sensor as in claim 4 wherein said means for measuring the deformation of said beam includes means for converting said deformation into an electrical signal.

7. A method for measuring vapor pressure by utilizing a vapor adsorbing material which expands on and contracts upon adsorption and desorption of vapor and by the use of a rigid substrate comprising forming a cantilevered beam in the substrate with a surface and adjoining the substrate to form a junction, forming the vapor adsorbing material as a thin layer of substantially uniform thickness on the surface of the cantilevered beam so that the layer is firmly adhered to the cantilevered beam and is shear restrained by the cantilevered beam and measuring the strain produced in the substrate at said junction by the stress applied by said layer to the cantilevered beam as said layer adsorbs and desorbs vapor.

8. A method as in claim 7 together with the step of providing a substrate formed of silicon.

* * * * *